United States Patent
Lindner et al.

(10) Patent No.: US 9,656,964 B2
(45) Date of Patent: May 23, 2017

(54) METHOD FOR PRODUCING CARBOXAMIDES

(71) Applicant: BAYER CROPSCIENCE AG, Monheim (DE)

(72) Inventors: Werner Lindner, Cologne (DE); Sergii Pazenok, Solingen (DE); Frank Volz, Cologne (DE)

(*) Notice: Subject to any disclaimer, the term of this patent is extended or adjusted under 35 U.S.C. 154(b) by 0 days.

(21) Appl. No.: 14/442,363

(22) PCT Filed: Nov. 8, 2013

(86) PCT No.: PCT/EP2013/073378
§ 371 (c)(1),
(2) Date: May 12, 2015

(87) PCT Pub. No.: WO2014/076007
PCT Pub. Date: May 22, 2014

(65) Prior Publication Data
US 2016/0009655 A1 Jan. 14, 2016

Related U.S. Application Data

(60) Provisional application No. 61/735,681, filed on Dec. 11, 2012.

(30) Foreign Application Priority Data

Nov. 13, 2012 (EP) .................................. 12356026

(51) Int. Cl.
*C07D 231/14* (2006.01)

(52) U.S. Cl.
CPC .................. *C07D 231/14* (2013.01)

(58) Field of Classification Search
CPC .................................................. C07D 231/14
See application file for complete search history.

(56) References Cited

U.S. PATENT DOCUMENTS

| 7,919,632 B2 | 4/2011 | Neeff et al. ............... 548/374.1 |
| 8,053,572 B2 | 11/2011 | Straub ............................ 544/63 |
| 8,088,927 B2 | 1/2012 | Mansfield et al. ............ 548/122 |
| 2010/0286221 A1* | 11/2010 | Mansfield ............ C07D 207/34 514/406 |
| 2012/0065164 A1 | 3/2012 | Bartels et al. .................. 514/63 |

FOREIGN PATENT DOCUMENTS

| DE | WO 2010130767 A2 * | 11/2010 | ........... C07D 231/16 |
| WO | WO 2006/092291 A2 | 9/2006 | |
| WO | WO 2006/136287 A1 | 12/2006 | |
| WO | WO 2007/087906 A1 | 8/2007 | |
| WO | WO 2010/130767 A1 | 11/2010 | |

OTHER PUBLICATIONS

International Search Report issued Dec. 5, 2013 in corresponding International Application No. PCT/EP2013/073378.

* cited by examiner

*Primary Examiner* — Michael Barker
*Assistant Examiner* — Amanda L Aguirre
(74) *Attorney, Agent, or Firm* — Morrison & Foerster LLP

(57) ABSTRACT

The present invention relates to a process for the preparation of carboxamide derivatives of formula (I) R N O N N CF2H C H3F

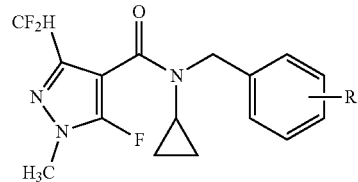

starting from 1-methyl-3-difluormethyl-.5-fluoro-1H-pyrazole-4-carbonyl halides in absence of an acid acceptor.

3 Claims, No Drawings

METHOD FOR PRODUCING CARBOXAMIDES

CROSS-REFERENCE TO RELATED APPLICATION(S)

The present application is a 35 U.S.C. §371 national phase conversion of PCT/EP2013/073378 filed on Nov. 8, 2013, which claims priority of European Application No. 12356026.0 filed on Nov. 13, 2012 and U.S. Provisional Application No. 61/735,681 filed on Dec. 11, 2012. Applicants claim priority to each of the foregoing applications. The PCT International Application was published in the English language.

FIELD OF THE INVENTION

The present invention relates to a novel process for preparing known fungicidally active cyclopropamides from the corresponding pyrazolic acid halides and cyclopropylamines derivatives in the absence of an acid acceptor.

BACKGROUND OF THE INVENTION

It is known from the International application WO2010/130767 that N-cycloalkyl-benzyl-amide derivatives can be obtained by reacting the corresponding acid chloride with the desired cyclopropylamines derivatives in the presence of an acid binder.

It is also known from the International patent application WO2007/087906 that N-cycloalkyl-henzyl-amide derivatives can be obtained by reacting the corresponding acid chloride with the desired cyclopropylamines derivatives Nevertheless said document does not specifically disclose a process in the absence of an acid binder.

It is also known from the International patent application WO2006/136287 that 5-fluoro-1,3-dimethyl-1H-pyrazole-4-carbonyl fluoride can react in the absence of acid acceptors with different aniline derivatives to form the corresponding carboxyamides. The reaction was possible without any acid acceptors because the week acid (HF) formed during the reaction did not produce salts with low basic anilines and the reaction can go to completion.

Nevertheless, the utilization of the axillary bases (acid acceptors) like $NEt_3$, Py or inorganic bases like NaOH is usually mandatory for the formation of amides obtained from acid halides and amines (Schotten-Baum process). In many cases the excess of the amines, used for the formation of the amide, can be used as well for trapping of the formed acid. The utilization of the additional base make the process more expensive.

SUMMARY OF THE INVENTION

It has now been found that carboxamides of the formula (I)

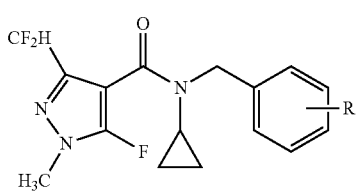

(I)

wherein R is selected from the list of 2-isopropyl, 2-cyclopropyl, 2-tert-butyl, 5-chloro-2-ethyl, 5-chloro-2-isopropyl, 2-ethyl-5-fluoro, 5-fluoro-2-isopropyl, 2-cyclopropyl-5-fluoro, 2-cyclopentyl-5-fluoro, 2-fluoro-6-isopropyl, 2-ethyl-5-methyl, 2-isopropyl-5-methyl, 2-cyclopropyl-5-methyl, 2-tert-butyl-5-methyl, 5-chloro-2-(trifluoromethyl), 5-methyl-2-(trifluoromethyl), 2-chloro-6-(trifluoromethyl), 3-chloro-2-fluoro-6-(trifluoromethyl) and 2-ethyl-4,5-dimethyl, can be prepared by reacting 1-methyl-3-difluormethyl-5-fluoro-1H-pyrazole-4-carbonyl halides of the formula (II)

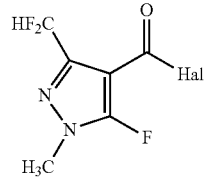

(II)

wherein Hal is F, Cl or Br,
with amines derivatives of the formula (III)

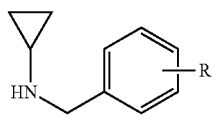

(III)

in which R is as defined above,
in the absence of an acid acceptor (also called acid binder).

In the context of the invention, "in the absence of an acid acceptor" means "in the absence of an acid acceptor other than the amine reactant (III)" or "in the absence of an additional acid acceptor" wherein "additional" means in addition to the amine derivative of the formula (III) which is part of the reaction.

Amines can be used also in the form of their salts of the formula (IY)

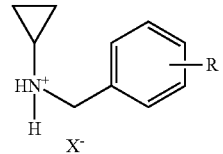

IY wherein X is F, Cl, Br, J, $HSO_4$, CH3COO, BF4, CH3SO3, CF3COO or CF3SO3.

DETAILED DESCRIPTION OF THE INVENTION

Surprisingly, the carboxamides of the formula (I) can be prepared under the inventive conditions with good yields in high purity and selectivity. A further advantage of the process according to the invention is that the workup is simpler, since an acid acceptor is not needed. This causes no waste water, an easier purification process without prior isolation by addition of an aliphatic alcohol in the same reaction vessel, and the process can be run in a higher concentration up to 50-70 w.w. %.

The resulting product has been obtained with a surprising purity superior to 95% or even close to 100%, and with less reagent and effort, while prior conditions in presence of an acid acceptor generally leads to a purity close to (or less than) 85-90%. Said surprising purity may be due to the absence of side products like pyrazolic acid made via hydrolysis of acid chloride in the presence of an acid acceptor, or derived from the substitution of the very reactive fluorine in the position 5 by acid acceptor like NEt3, NaOH, K2CO3. The absence of said side products increases the purity of the final product and make the purification less complex and difficult.

Additionally, the process without an acid acceptor is surprisingly less sensitive to the impurities present in the amines (e.g. moisture or alcohols coming from the previous steps). Said surprising effect may be due to the fact that these impurities do not react with acid chloride under the inventive conditions and do not affect the purity of the final product. The advantageous consequence is that amines with low purity could be still successfully used for the production of carboxamides of the formula (I) making the process according to the invention more economically valuable and simple.

When, for example, 1-methyl-3-difluoromethyl-5-fluoro-1H-pyrazole-4-carbonyl chloride and N-(2-isopropyl-5-chloro-benzyl)cyclopropylamine are used as starting materials, the process according to the invention can be illustrated by the following formula scheme:

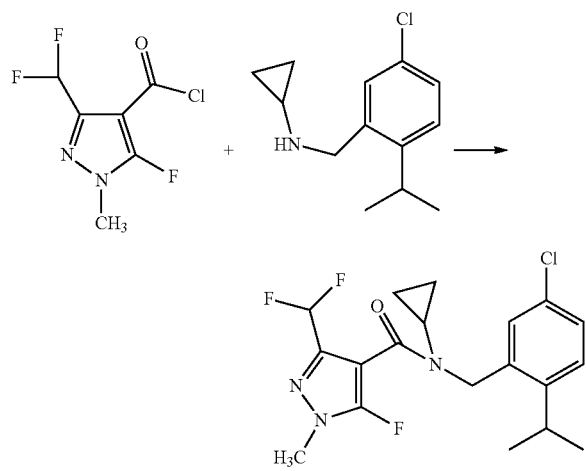 [SMILES: Cn1nc(C(F)F)c(C(=O)Cl)c1F ; CC(C)c1ccc(Cl)cc1CNC1CC1 ; CC(C)c1ccc(Cl)cc1CN(C(=O)c1c(C(F)F)nn(C)c1F)C1CC1]

The 1-methyl-3-difluoromethyl-5-fluoro-1H-pyrazole-4-carbonyl chloride and fluoride of the formula (II) used as a starting material in the performance of the process according to the invention are known (WO 2011131615; WO 2011061205).

Preference is given in the use of amines of the formula (III-1) or its salt (IY-1)

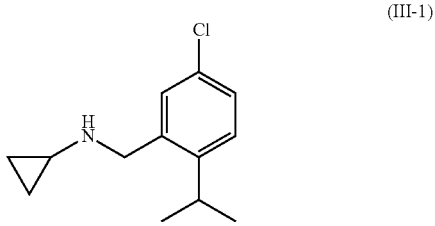

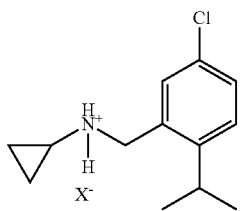

The process according to the invention is preferably used to prepare one compound of formula (I) selected from the group consisting of:
N-cyclopropyl-3-(difluoromethyl)-5-fluoro-N-(2-isopropylbenzyl)-1-methyl-1H-pyrazole-4-carboxamide,
N-cyclopropyl-N-(2-cyclopropylbenzyl)-3-(difluoromethyl)-5-fluoro-1-methyl-1H-pyrazole-4-carboxamide,
N-(2-tert-butylbenzyl)-N-cyclopropyl-3-(difluoromethyl)-5-fluoro-1-methyl-1H-pyrazole-4-carboxamide,
N-(5-chloro-2-ethylbenzyl)-N-cyclopropyl-3-(difluoromethyl)-5-fluoro-1-methyl-1H-pyrazole-4-carboxamide,
N-(5-chloro-2-isopropylbenzyl)-N-cyclopropyl-3-(difluoromethyl)-5-fluoro-1-methyl-1H-pyrazole-4-carboxamide,
N-cyclopropyl-3-(difluoromethyl)-N-(2-ethyl-5-fluorobenzyl)-5-fluoro-1-methyl-1H-pyrazole-4-carboxamide,
N-cyclopropyl-3-(difluoromethyl)-5-fluoro-N-(5-fluoro-2-isopropylbenzyl)-1-methyl-1H-pyrazole-4-carboxamide,
N-cyclopropyl-N-(2-cyclopropyl-5-fluorobenzyl)-3-(difluoromethyl)-5-fluoro-1-methyl-1H-pyrazole-4-carboxamide,
N-(2-cyclopentyl-5-fluorobenzyl)-N-cyclopropyl-3-(difluoromethyl)-5-fluoro-1-methyl-1H-pyrazole-4-carboxamide,
N-cyclopropyl-3-(difluoromethyl)-5-fluoro-N-(2-fluoro-6-isopropylbenzyl)-1-methyl-1H-pyrazole-4-carboxamide,
N-cyclopropyl-3-(difluoromethyl)-N-(2-ethyl-5-methylbenzyl)-5-fluoro-1-methyl-1H-pyrazole-4-carboxamide,
N-cyclopropyl-3-(difluoromethyl)-5-fluoro-N-(2-isopropyl-5-methylbenzyl)-1-methyl-1H-pyrazole-4-carboxamide,
N-cyclopropyl-N-(2-cyclopropyl-5-methylbenzyl)-3-(difluoromethyl)-5-fluoro-1-methyl-1H-pyrazole-4-carboxamide,
N-(2-tert-butyl-5-methylbenzyl)-N-cyclopropyl-3-(difluoromethyl)-5-fluoro-1-methyl-1H-pyrazole-4-carboxamide,
N-[5-chloro-2-(trifluoromethyl)benzyl]-N-cyclopropyl-3-(difluoromethyl)-5-fluoro-1-methyl-1H-pyrazole-4-carboxamide (compound A15),
N-cyclopropyl-3-(difluoromethyl)-5-fluoro-1-methyl-N-[5-methyl-2-(trifluoromethyl)benzyl]-1H-pyrazole-4-carboxamide (compound A16),
N-[2-chloro-6-(trifluoromethyl)benzyl]-N-cyclopropyl-3-(difluoromethyl)-5-fluoro-1-methyl-1H-pyrazole-4-carboxamide,
N-[3-chloro-2-fluoro-6-(trifluoromethyl)benzyl]-N-cyclopropyl-3-(difluoromethyl)-5-fluoro-1-methyl-1H-pyrazole-4-carboxamide.
N-cyclopropyl-3-(difluoromethyl)-N-(2-ethyl-4,5-dimethylbenzyl)-5-fluoro-1-methyl-1H-pyrazole-4-carboxamide,
and N-cyclopropyl-3-(difluoromethyl)-5-fluoro-N-(2-isopropylbenzyl)-1-methyl-1H-pyrazole-4-carbothio-amide.

Amines derivatives of the formula (IR) and their salts are known or can be prepared in a known manner The process according to the invention can be performed in the presence of a diluent. Useful diluents for this purpose include all inert organic solvents, preferably aliphatic, alicyclic or aromatic hydrocarbons, for example petroleum ether, hexane, heptane, cyclohexane, methylcyclohexane, benzene, toluene, xylene or decalin; halogenated hydrocarbons, for example chlorobenzene, dichlorobenzene, dichloromethane, chloroform, tetrachloromethane, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; ketones such as acetone, butanone, methyl isobutyl ketone or cyclohexanone; nitriles such as acetonitrile, propionitrile, n- or i-butyronitrile or benzonitrile; amides such as N,N-dimethylformamide, N,N-dimethylacetamide, N-methylformanilide, N-methylpyrrolidone or hexamethylphosphoramide, more preferably are used chlorobenzene and toluene.

The reaction temperatures in the performance of the process according to the invention can be varied within a relatively wide range. In general, temperatures of from 70° C. to 150° C., preferably temperatures of from 80° C. to 140° C., are employed.

In the performance of the process according to the invention, generally between 0.8 and 1.5 mol, preferably equimolar amounts, of amines derivatives of the formula (III) and (IV) are used per mole of the 1-methyl-3-difluoromethyl-5-fluoro-1H-pyrazole-4-carbonyl halides of the formula (II).

Depending on the reactivity of the reactants, the reaction time may be up to 15 hours, but the reaction can also be terminated even earlier in the case of complete conversion. Preference is given to reaction times of 5-10 hours.

All processes according to the invention are generally performed under standard pressure. However, it is possible to work under elevated or reduced pressure—generally between 0.1 bar and 10 bar.

For the work up it is enough to remove the solvent and precipitate the formed product. It is also possible to extract the product and wash the solution with water. In all cases the product was formed in purity more than 95% so any further purification was not needed.

The inventive preparation of carboxamides of the formula (I) is described in the examples which follow, which further illustrate the above description. However, the examples should not be interpreted in a restrictive manner.

PREPARATION EXAMPLES

Preparation Example: N-(2-isopropyl-5-chlorolbenzyl)-N-cyclopropyl-5-fluoro-1-methyl-3-difluoromethyl-1H-pyrazole-4-carboxamide Under protective gas (argon), a solution of N-(2-isopropyl-5-chloro-benzyl)cyclopropylamine 22.4 g (100 mmol) in 100 ml of chlorobenzene is initially charged. 21.2 g (100 mmol) of 1-methyl-3-difluoromethyl-5-fluoro-1H-pyrazole-4-carbonyl chloride are added and the mixture is stirred at 100° C. for 8 h. For workup, the solvent was removed in vacuum and the residue was washed with 50 ml of cold isopropanol to give 37 g (93% of theory) carboxamide in the form of white crystals with melting point of 108-110° C.

Preparation Example: N-(4-trifluoromethyl-benzyl)-N-cyclopropyl-5-fluoro-1,3-dimethyl-1H-pyrazole-4-carboxamide A solution of 25 g of N-(4-trifluoromethyl-benzyl)cyclopropylamine hydrochloride, 17 g of 5-fluoro-1,3-dimethyl-1H-pyrazole-4-carbonyl chloride were heated in 200 ml Toluene at 100° C. for 8 h. Solvent is removed under reduced pressure. Residue was washed with 50 ml of cold isopropanol. to yield 31 g of desired N-(4-trifluoromethyl-benzyl)-N-cyclopropyl-5-fluoro-1,3-dimethyl-1H-pyrazole-4-carboxamide as a white solid (Log P=2.8).

Similar Prepared

N-cyclopropyl-3-(difluoromethyl)-5-fluoro-N-(2-isopropylbenzyl)-1-methyl-1H-pyrazole-4-carboxamide, yield 93%.

N-cyclopropyl-N-(2-cyclopropylbenzyl)-3-(difluoromethyl)-5-fluoro-1-methyl-1H-pyrazole-4-carboxamide, yield 95%.

N-(2-tert-butylbenzyl)-N-cyclopropyl-3-(difluoromethyl)-5-fluoro-1-methyl-1H-pyrazole-4-carboxamide, yield 93%.

N-(5-chloro-2-ethylbenzyl)-N-cyclopropyl-3-(difluoromethyl)-5-fluoro-1-methyl-1H-pyrazole-4-carboxamide, yield 89%.

N-(5-chloro-2-isopropylbenzyl)-N-cyclopropyl-3-(difluoromethyl)-5-fluoro-1-methyl-1H-pyrazole-4-carboxamide yield 97%.

The invention claimed is:

1. Process for the preparation of carboxamide derivatives of formula (I)

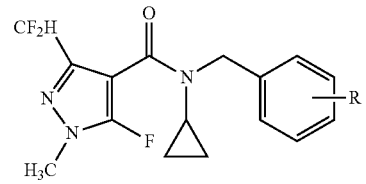

wherein R is selected from the list of 2-isopropyl, 2-cyclopropyl, 2-tert-butyl, 5-chloro-2-ethyl, 5-chloro-2-isopropyl, 2-ethyl-5-fluoro, 5-fluoro-2-isopropyl, 2-cyclopropyl-5-fluoro, 2-cyclopentyl-5-fluoro, 2-fluoro-6-isopropyl, 2-ethyl-5-methyl, 2-isopropyl-5-methyl, 2-cyclopropyl-5-methyl, 2-tert-butyl-5-methyl, 5-chloro-2-(trifluoromethyl), 5-methyl-2-(trifluoromethyl), 2-chloro-6-(trifluoromethyl), 3-chloro-2-fluoro-6-(trifluoromethyl) and 2-ethyl-4,5-dimethyl, characterized in that 1-methyl-3-difluormethyl-5-fluoro-1H-pyrazole-4-carbonyl halides of the formula (II)

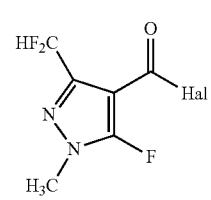

in which Hal is F, Cl or Br,
are reacted with amine derivatives of the formula (III) or (IY)

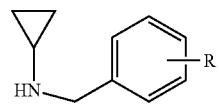

-continued

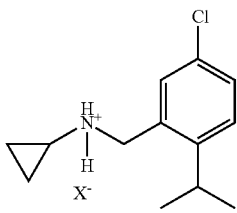
(IY)

in which
R is as defined above,
X is F, Cl, Br, J, $HSO_4$, $CH_3COO$, $BF_4$, $CH_3SO_3$, $CF_3COO$ or $CF_3SO_3$,
in the absence of an acid acceptor other than an amine of formula (III) or (IY), and wherein between 0.8 and 1.5 mol of amine derivatives are used per mol of the compound of formula (II).

2. Process according to claim 1, wherein the amine derivatives are of formula (III-1)

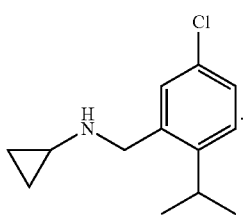
(III-1)

3. Process according to claim 1 for the preparation of a carboxamide derivatives selected from the group consisting of:
N-cyclopropyl-3-(difluoromethyl)-5-fluoro-N-(2-isopropylbenzyl)-1-methyl-1H-pyrazole-4-carboxamide (compound A1),
N-cyclopropyl-N-(2-cyclopropylbenzyl)-3-(difluoromethyl)-5-fluoro-1-methyl-1H-pyrazole-4-carboxamide (compound A2),
N-(2-tert-butylbenzyl)-N-cyclopropyl-3-(difluoromethyl)-5-fluoro-1-methyl-1H-pyrazole-4-carboxamide (compound A3),
N-(5-chloro-2-ethylbenzyl)-N-cyclopropyl-3-(difluoromethyl)-5-fluoro-1-methyl-1H-pyrazole-4-carboxamide (compound A4),
N-(5-chloro-2-isopropylbenzyl)-N-cyclopropyl-3-(difluoromethyl)-5-fluoro-1-methyl-1H-pyrazole-4-carboxamide (compound A5),
N-cyclopropyl-3-(difluoromethyl)-N-(2-ethyl-5-fluorobenzyl)-5-fluoro-1-methyl-1H-pyrazole-4-carboxamide (compound A6),
N-cyclopropyl-3-(difluoromethyl)-5-fluoro-N-(5-fluoro-2-isopropylbenzyl)-1-methyl-1H-pyrazole-4-carboxamide (compound A7),
N-cyclopropyl-N-(2-cyclopropyl-5-fluorobenzyl)-3-(difluoromethyl)-5-fluoro-1-methyl-1H-pyrazole-4-carboxamide (compound A8),
N-(2-cyclopentyl-5-fluorobenzyl)-N-cyclopropyl-3-(difluoromethyl)-5-fluoro-1-methyl-1H-pyrazole-4-carboxamide (compound A9),
N-cyclopropyl-3-(difluoromethyl)-5-fluoro-N-(2-fluoro-6-isopropylbenzyl)-1-methyl-1H-pyrazole-4-carboxamide (compound A10),
N-cyclopropyl-3-(difluoromethyl)-N-(2-ethyl-5-methylbenzyl)-5-fluoro-1-methyl-1H-pyrazole-4-carboxamide (compound A11),
N-cyclopropyl-3-(difluoromethyl)-5-fluoro-N-(2-isopropyl-5-methylbenzyl)-1-methyl-1H-pyrazole-4-carboxamide (compound A12),
N-cyclopropyl-N-(2-cyclopropyl-5-methylbenzyl)-3-(difluoromethyl)-5-fluoro-1-methyl-1H-pyrazole-4-carboxamide (compound A13),
N-(2-tert-butyl-5-methylbenzyl)-N-cyclopropyl-3-(difluoromethyl)-5-fluoro-1-methyl-1H-pyrazole-4-carboxamide (compound A14),
N-[5-chloro-2-(trifluoromethyl)benzyl]-N-cyclopropyl-3-(difluoromethyl)-5-fluoro-1-methyl-1H-pyrazole-4-carboxamide (compound A15),
N-cyclopropyl-3-(difluoromethyl)-5-fluoro-1-methyl-N-[5-methyl-2-(trifluoromethyl)benzyl]-1H-pyrazole-4-carboxamide (compound A16),
N-[2-chloro-6-(trifluoromethyebenzyl]-N-cyclopropyl-3-(difluoromethyl)-5-fluoro-1-methyl-1H-pyrazole-4-carboxamide (compound A17),
N-[3-chloro-2-fluoro-6-(trifluoromethyl)benzyl]-N-cyclopropyl-3-(difluoromethyl)-5-fluoro-1-methyl-1H-pyrazole-4-carboxamide (compound A18),
N-cyclopropyl-3-(difluoromethyl)-N-(2-ethyl-4,5-dimethylbenzyl)-5-fluoro-1-methyl-1H-pyrazole-4-carboxamide (compound A19), and
N-cyclopropyl-3-(difluoromethyl)-5-fluoro-N-(2-isopropylbenzyl)-1-methyl-1H-pyrazole-4-carbothio-amide (compound A20).

* * * * *